US00PP13819P29

(12) United States Plant Patent
Janick et al.

(10) Patent No.: US PP13,819 P2
(45) Date of Patent: May 13, 2003

(54) APPLE TREE NAMED 'CO-OP 29'

(75) Inventors: Jules Janick, West Lafayette, IN (US); Edwin B. Williams, Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 10/032,052

(22) Filed: Dec. 21, 2001

(51) Int. Cl.[7] ..... A01H 5/00
(52) U.S. Cl. ..... Plt./172
(58) Field of Search ..... Plt./172, 161

(56) References Cited

U.S. PATENT DOCUMENTS

PP7,618 P * 8/1991 Luginbuhl ..... Plt./172
PP9,881 P * 5/1997 Janick et al. ..... Plt./172

OTHER PUBLICATIONS

Internet web pages, "Pedigree, A Genetic Resource Inventory System," http://www.universaldbase.com/pgris/pedigree/1st–app.html, originally found on website on Sep. 6, 2002, pp. 1–5.*

* cited by examiner

*Primary Examiner*—Bruce R. Campell
*Assistant Examiner*—Susan B. McCormick
(74) *Attorney, Agent, or Firm*—Klarquist Sparkman, LLP

(57) ABSTRACT

A new apple variety distinguished by good storage ability, good to excellent dessert quality, and a resistance to apple scab, cedar rust, and fireblight, with a moderate resistance to powdery mildew.

1 Drawing Sheet

LATIN NAME OF THE GENUS AND SPECIES OF THE PLANT CLAIMED

*Malus×domestica.*

VARIETY DENOMINATION

'Co-op 29'.

BACKGROUND OF THE INVENTION

The present invention relates to a new and distinct variety of apple tree narned 'Co-op 29'. Our new tree resulted from a planned hybridization program and is a selection from crossing 'Golden Delicious' (unpatented) as the seed parent with '1050 NJI', an unpatented apple tree, as the pollen parent. The resulting tree was selected when growing in a cultivated area in West Lafayette, Ind.

BRIEF SUMMARY OF THE INVENTION

The 'Co-op 29' variety is distinguished from other apple varieties due to the following unique combination of characteristics: resistance to apple scab; resistance to cedar rust and fireblight; moderately resistant to powdery mildew; good storage ability (can be stored up to seven months at 34° F.); and good to excellent dessert quality.

Asexual reproduction of this new variety by grafting and budding onto rootstock ['Malling 7' (unpatented) and 'Malling Merton 111' (unpatented) rootstocks] shows that the foregoing characteristics come true to form, are firmly fixed, and are established and transmitted through succeeding propagations.

The following detailed description concerns the original tree, discovered in 1972, and progeny first asexually propagated in 1979. The original tree and progeny have been observed growing in a cultivated area in West Lafayette, Ind. Certain characteristics of this variety, such as growth and color, may change with changing environmental conditions (e.g., light, temperature, moisture, nutrient availability, or other factors). Color descriptions and other terminology are used in accordance with their ordinary dictionary descriptions, unless the context clearly indicates otherwise. Color designations are made with reference to The Royal Horticultural Society (R.H.S.) Colour Chart.

BRIEF DESCRIPTION OF THE DRAWING

The accompanying photograph shows typical fruit and leaf specimens of this new variety.

The colors of an illustration of this type may vary with lighting and other conditions under which conditions and, therefore, color characteristics of this new variety should be determined with reference to the observations described herein, rather than from these illustrations alone.

DETAILED BOTANICAL DESCRIPTION

The following detailed description of the 'Co-op 29' variety is based on observations of asexually reproduced progeny. The observed progeny are trees which were 13 years of age and growing on 'Malling Merton 111' rootstock in West Lafayette, Ind.

Scientific name: *Malus×domestica* 'Co-op 29'.
Parentage:
*Seed parent.*—'Golden Delicious' (unpatented).
*Pollen parent.*—'1050 NJI' (unpatented), which resulted from a cross of the 'Winter Banana' variety (unpatented) and the 'PRI 2-19' variety (unpatented).
Tree:
*Vigor.*—Moderate.
*Overall shape.*—Upright.
*Height.*—About 12 to about 15 feet.
*Width.*—Overall spread of about 10 to about 12 feet.

*Caliper.*—6 inches at 14 inches above ground.
*Trunk.*—Slender.
*Trunk bark texture.*—Smooth to slightly rough.
*Trunk bark color.*—Grey-green (RHS 197A).
*Patches or other markings.*—Slightly scaly; scales are grey-green (RHS 201B) in color.
*Primary branches.*—Spreading; branches emerge at an angle of about 30 to 35 degrees; the angle of emergence increases with the height of the tree; no included bark has been observed.
*Branch color.*—One-year old branches are grey-red (RHS 178B) in color, while two-year old branches are grey-green (RHS 199A) in color.
*Branch pubescence.*—A slight amount of pubescence occurs at the tip of one-year wood.
*New growth bark.*—Grey-green (RHS 192D) in color.
*Branch lenticels.*—Medium density, approximately 80 per square inch; round, typical examples of which measured about 0.05 inch in diameter; white (RHSN 155C) in color.
*Internodes.*—Average internode length is about 1.1 inch on a one-year old shoot.
*Bearing.*—Slightly biennial.
*Hardiness.*—Zones 5 to 7, comparable to 'Golden Delicious.'
*Disease resistance.*—Field immune to apple scab; resistant to Cedar Apple Rust and fireblight; moderately tolerant to powdery mildew.

Leaves:
*Texture.*—Smooth, Medium thick.
*Sheen.*—Dull.
*Length.*—About 2.5 inches to about 4.2 inches, averaging about 3.4 inches.
*Width.*—About 1.6 inches to about 2.2 inches, averaging about 1.9 inches.
*Thickness.*—About 0.004 inch to about 0.011 inch, averaging about 0.007 inches.
*Petiole.*—About 1.4 inches long; yellow-green in color; about 0.04 inch in diameter; pubescent.
*Margin.*—Serrate.
*Tip shape.*—Acute.
*Stipules.*—Two stipules in opposite arrangement; green-red (RHS 64B) in color; strap-like shape, length about 0.29 inch long and about 0.04 inch wide.
*Leaf color.*—Upper leaf surface: Green (RHS 137B). Lower leaf surface: Yellow-green (RHS 148A). Vein: Yellow-green (RHS 154D).
*Pubescence.*—Fine pubescence observed on the lower leaf surface of young leaves; substantially white in color. The length, width, thickness and other measurements were obtained from observations of ten typical leaves in October of 2001.

Flowers:
*Size.*—Medium size, typical flower measuring about 4.9 mm across.
*Color.*—Unopened bud: Pink-red (RHS 49A). Opened flower: Petal color is white, (RHS N155A), on both sides.
*Bud length* (*expanded pink*).—10.2 mm.
*Bud diameter* (*tight pink*).—7 mm.
*Petal shape.*—Base: slightly acuminate; Apex: rounded.
*Petals.*—Five petals per flower; round to oval in shape; about 0.8 (to slightly larger) inch long and 0.8 (to slightly smaller) inch wide; barely touching at full bloom.
*Stamen.*—Arranged in a single row. Twenty stamens, each about 7–9 mm long and white in color.
*Anthers.*—Yellow-orange (RHS 17C) in color.
*Pistil.*—Stigma is about 7–9 mm long; five styles, fused at base, and yellow-green (RHS 154C) in color.
*Sepals.*—About 8 to 9 mm and about 4 to 5 mm wide; recurved shape; yellow-green (RHS 150A) in color; moderate pubescence.
*Pollen.*—Yellow-orange (RHS 17C) in color.
*Fragrance.*—Slight.
*Bloom season.*—75% full bloom observed on Apr. 22, 2001.

Pedicel:
*Length.*—18.0 mm.
*Diameter.*—1.5 mm. Color is green (RHS 142C).

Fruit: (Observations from a limited number of typical fruit in October of 2001.)
*Size.*—Small, about 2.7 inches long and 3.0 inches wide; box size of about 88 to 100.
*Form.*—Round to conic; symmetrical; typical length to diameter ratio of about 0.9 in 2001; no ribbing; no lobes observed at calyx end.
*Cavity.*—Average narrowness, deep; cavity is about 0.7 inch deep and slightly less than about 1.0 inch wide.
*Basin.*—About 0.28 inch deep and about 0.76 inch wide; pubescence observed on the calyx.
*Stem.*—Short, medium thickness; typical average observed in 2001, about 0.72 inch long and 0.075 inch in diameter; grey-yellow (R.H.S. 161A) in color.
*Locules.*—Five small, closed locules; seeds are free of the carpel wall at maturity.
*Skin.*—Thin and glossy with no tendency to become waxy or oily in storage.
*Lenticels.*—Inconspicuous, appear as minute round dots, yellow-green in color (RHS 149C).
*Color.*—General color effect: Green-yellow to yellow with a slight orange-red blush. Ground color: Green-yellow (RHS 1C); color intensifies toward yellow at maturity between dates of first and last picking. Overcolor: Mottled orange-red (RHS 34D) blush that can be conspicuous. Russetting: Present on stem and can radiate from the cavity.
*Fruit properties at maturity* (*based on five fruit tested in October of* 2001).—Acid content: About 0.44 g/100 ml malic acid. Firmness: About 7.4 to 8.9 kg, averaging about 7.8 kg. Soluble solids: About 11.0 to 13.9%, averaging about 12.4%. Starch index: On a scale of 1 (high starch) to 9 (low starch), range 7 to 9, average about 7.6. Flavor: Mild., Juiciness: Medium juicy. Flesh color: Yellow-white (RHS 158D). Aroma: Very slight.
*Core.*—Median bundle area shape; typical in 2001 about 0.89 inch long and about 0.87 inch wide; closed calyx tube measuring about 0.11 inch long; core lines weakly defined.
*Seed.*—About 1–2 seeds per cell; acutely shaped; about 0.35 inch long and about 0.18 inch wide; grey-red (RHS 178B) in color.
*Fruit production.*—First picking date in 2001 in Lafayette, Ind. was about October 10, and last picking date was about October 17; average production is 320 lbs. of fruit per tree.
*Storage.*—Fruit remains fresh at room temperature for 5–7 days, and can be stored up to seven months in cold storage (34° F.).

*Usage.*—Dessert, juice, apple butter, apple sauce.

*Fruit weight.*—(based on a single fruit with a 2.9 inch diameter×2.5 inch height tested in October 2002) 172 g.

We claim:

1. A new and distinct variety of apple tree, substantially as herein shown and described.

* * * * *

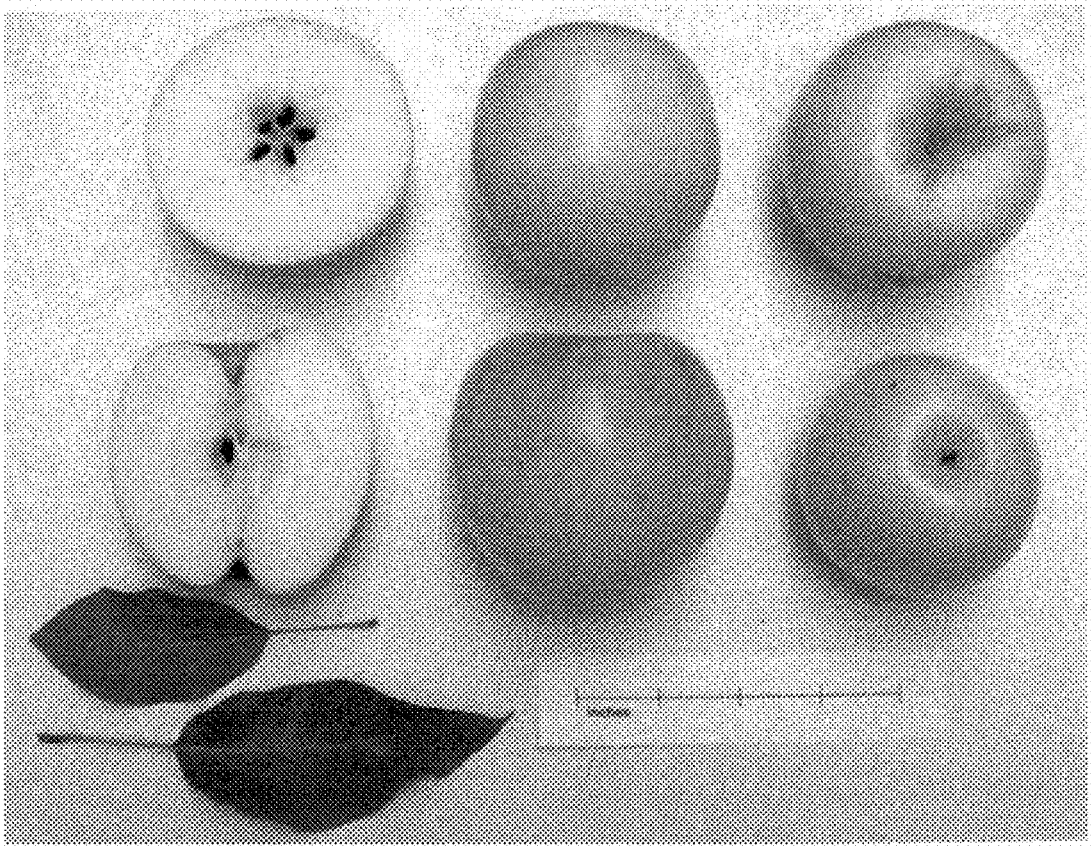

UNITED STATES PATENT AND TRADEMARK OFFICE
Certificate

Patent No. PP13,819 P2

Patented: May 13, 2003

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Jules Janick, West Lafayette, IN (US); Edwin B. Williams, Lafayette, IN (US); Joseph C. Goffreda, Monmouth, NJ (US); and Schuyler S. Korban, Champaign, IL (US).

Signed and Sealed this Twenty-fifth Day of March 2008.

ANNE M. GRUNBERG
*Supervisory Patent Examiner*
Art Unit 1661